US00PP35199P3

(12) United States Plant Patent
Nebelmeir

(10) Patent No.: US PP35,199 P3
(45) Date of Patent: May 30, 2023

(54) POINSETTIA PLANT NAMED 'LAZZPO1531'

(50) Latin Name: ***Euphorbia pulcherrima* Willd.**
Varietal Denomination: LAZZPO1531

(71) Applicant: LAZZERI GENETICA S.A.S. di DALLAGO FRANCO & C., Merano (IT)

(72) Inventor: Johannes Nebelmeir, Hann (DE)

(73) Assignee: LAZZERI GENETICA S.A.S. di DALLAGO FRANCO & C., Merano (IT)

( * ) Notice: Subject to any disclaimer, the term of this patent is extended or adjusted under 35 U.S.C. 154(b) by 0 days.

(21) Appl. No.: 17/958,467

(22) Filed: Oct. 3, 2022

(65) Prior Publication Data

US 2023/0116918 P1 Apr. 13, 2023

Related U.S. Application Data

(60) Provisional application No. 63/251,807, filed on Oct. 4, 2021.

(51) Int. Cl.
*A01H 5/02* (2018.01)
*A01H 6/38* (2018.01)

(52) U.S. Cl.
USPC ..... Plt./307
CPC ..... *A01H 6/385* (2018.05)

(58) Field of Classification Search
USPC ..... Plt./307
CPC ..... A01H 6/385
See application file for complete search history.

(56) References Cited

PUBLICATIONS

CPVO hit on UPOV Plant Breeder's Rights for poinsettia plant named, 'LAZZPO1531', QZ PBR 20212516, application date Oct. 6, 2021.*

* cited by examiner

*Primary Examiner* — Anne Marie Grunberg
(74) *Attorney, Agent, or Firm* — C. Anne Whealy

(57) ABSTRACT

A new and distinct cultivar of Poinsettia plant named 'LAZZPO1531', characterized by its upright "V"-shaped and uniformly mounding plant habit; moderately vigorous to vigorous growth habit; freely branching habit and strong stems; dark green-colored leaves; full inflorescences with medium to large deep red-colored flower bracts; and excellent post-production longevity.

1 Drawing Sheet

Figure 1:
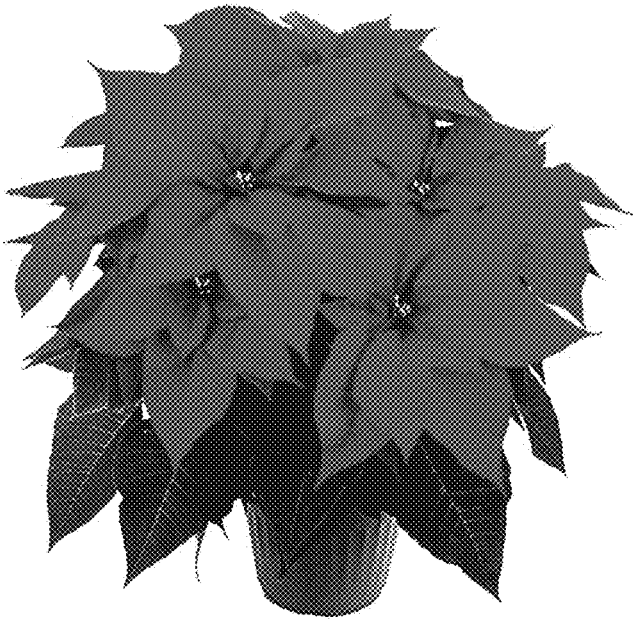

Botanical designation: *Euphorbia pulcherrima* Willd.
Cultivar denomination: 'LAZZPO1531'.

BACKGROUND OF THE INVENTION

The present invention relates to a new and distinct cultivar of Poinsettia plant, botanically known as *Euphorbia pulcherrima* Willd. and hereinafter referred to by the name 'LAZZPO1531'.

The new Poinsettia plant is a product of a planned breeding program conducted by the Inventor in Merano and Sabaudia, Italy. The objective of the breeding program is to create new upright "V"-shaped and freely-branching Poinsettia plants with strong stems and attractive flower bracts.

The new Poinsettia plant originated from a cross-pollination during the spring of 2012 in Merano, Italy of a proprietary selection of *Euphorbia pulcherrima* Willd. identified as code number 2007-606-005, not patented, as the female, or seed, parent with *Euphorbia pulcherrima* Willd. 'Allegra Red', not patented, as the male, or pollen parent. The new Poinsettia plant was discovered and selected by the Inventor as a single flowering plant from within the progeny of the stated cross-pollination grown in a controlled greenhouse environment in Sabaudia, Italy in December, 2013.

Asexual reproduction of the new Poinsettia plant by terminal vegetative cuttings in a controlled greenhouse environment in Sabaudia, Italy since July, 2014 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'LAZZPO1531'. These characteristics in combination distinguish 'LAZZPO1531' as a new and distinct Poinsettia plant:

1. Upright "V"-shaped and uniformly mounding plant habit.
2. Moderately vigorous to vigorous growth habit.
3. Freely branching habit and strong stems.
4. Dark green-colored leaves.
5. Full inflorescences with medium to large deep red-colored flower bracts.
6. Excellent post-production longevity.

Plants of the new Poinsettia can be compared to plants of the female parent selection. Plants of the new Poinsettia differ primarily from plants of the female parent selection in flower bract color as plants of the new Poinsettia have deeper red-colored flower bracts than plants of the female parent selection. In addition, plants of the new Poinsettia are smaller than plants of the female parent selection.

Plants of the new Poinsettia can be compared to plants of the male parent, 'Allegra Red'. Plants of the new Poinsettia differ primarily from plants of 'Allegra Red' in plant habit as plants of the new Poinsettia are smaller and more "V"-shaped than plants of 'Allegra Red'. In addition, plants of the new Poinsettia have stronger stems than plants of 'Allegra Red'.

Plants of the new Poinsettia can be compared to plants of *Euphorbia pulcherrima* Willd. 'BKPONLR', disclosed in U.S. Plant Pat. No. 29,012. In side-by-side comparisons, plants of the new Poinsettia differ primarily from plants of 'BKPONLR' in the following characteristics:

1. Plants of the new Poinsettia are uniformly mounding than plants of 'BKPONLR'.
2. Flower bracts of plants of the new Poinsettia are more drooping than flower bracts of plants of 'BKPONLR'.
3. Plants of the new Poinsettia flower about ten days later than plants of 'BKPONLR'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph at the top of the sheet (FIG. 1) is a side perspective view of a typical flowering plant of 'LAZZPO1531' grown in a container.

Figure 2:
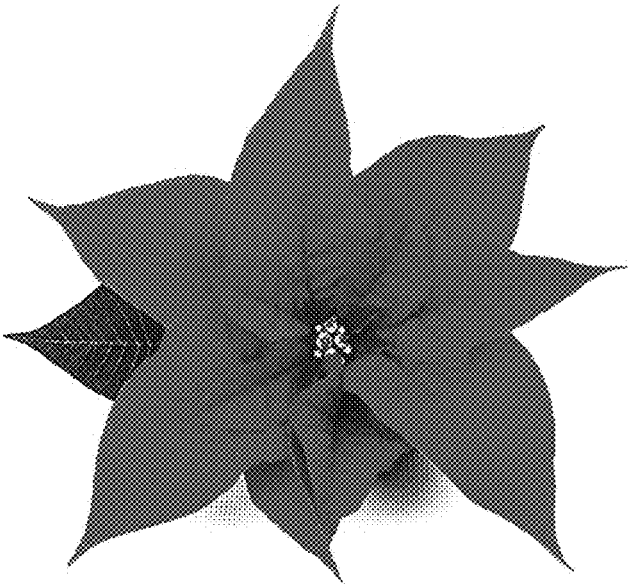

The photograph at the bottom of the sheet (FIG. 2) is a close-up view of a typical inflorescence of 'LAZZPO1531'.

DETAILED BOTANICAL DESCRIPTION

The aforementioned photographs and following observations and measurements describe plants grown during the autumn and winter in 14-cm containers in a glass-covered greenhouse in Merano, Italy and under cultural practices typical of commercial Poinsettia production. During the production of the plants, day temperatures ranged from 15° C. to 20° C., night temperatures ranged from 10° C. to 15° C. and light levels ranged from 40 to 55 klux. Plants were pinched one time after planting, grown under natural day-length conditions and were five months old when the photographs and the detailed description were taken. In the following description, color references are made to The Royal Horticultural Society Colour Chart, 1995 Edition, except where general terms of ordinary dictionary significance are used.

Botanical classification: *Euphorbia pulcherrima* Willd. 'LAZZPO1531'.

Parentage:

*Female, or seed, parent.*—Proprietary selection of *Euphorbia pulcherrima* Willd. identified as code number 2007-606-005, not patented.

*Male, or pollen, parent.*—*Euphorbia pulcherrima* Willd. 'Allegra Red', not patented.

Propagation:

*Type.*—Terminal vegetative cuttings.

*Time to initiate roots, summer.*—About two weeks at soil temperatures ranging from 22° C. to 25° C. and ambient temperatures ranging from 25° C. to 30° C.

*Time to produce a rooted young plant, summer.*—About 24 days at soil temperatures ranging from 22° C. to 25° C. and ambient temperatures ranging from 25° C. to 30° C.

*Root description.*—Medium to thick, slightly fleshy; typically pale creamy white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Upright "V"-shaped and uniformly mounding plant habit; moderately vigorous to vigorous growth habit and moderate to rapid growth rate; full inflorescences positioned above the foliar plane.

*Plant height, soil level to top of foliar plane.*—About 20 cm to 22 cm.

*Plant height, soil level to top of floral plane.*—About 24 cm to 26 cm.

*Plant diameter or spread.*—About 35 cm to 40 cm.

*Lateral branch description.*—Branching habit: Freely branching habit with about four to five lateral branches developing after pinching. Length: About 20 cm. Diameter: About 5 mm. Internode length: About 2 cm. Strength: Strong, sturdy. Texture and luster: Smooth, glabrous; glossy. Color, developing: Close to 137D; at the internodes, close to 137B. Color, developed: Close to 146B.

*Leaf description.*—Arrangement: Alternate, simple. Length: About 12 cm to 13 cm. Width: About 8 cm. Shape: Ovate. Apex: Acuminate. Base: Cuneate. Margin: Entire; slightly undulate. Venation pattern: Pinnate, reticulate. Texture and luster, upper surface: Smooth, glabrous; semi-glossy. Texture and luster, lower surface: Smooth, glabrous; matte. Color: Developing leaves, upper surface: Close to 143A. Developing leaves, lower surface: Close to 143B. Fully expanded leaves, upper surface: Close to 137A; venation, close to 147B. Fully expanded leaves, lower surface: Close to 146D; venation, close to 146D. Petioles: Length: About 4 cm to 6 cm. Diameter: About 3 mm to 4 mm. Strength: Moderately strong. Texture and luster, upper and lower surfaces: Smooth, glabrous; glossy. Color, upper surface: Close to 146A. Color, lower surface: Close to 147B.

Inflorescence description:

*Inflorescence type and habit.*—Full inflorescences are compound corymbs of cyathia with colored flower bracts subtending the cyathia; one inflorescence per lateral branch with inflorescences positioned above and beyond the foliar plane.

*Fragrance.*—None detected.

*Natural flowering season.*—Plants flower naturally during the late autumn to winter under long nycto-period conditions; inflorescence initiation and development can be induced under artificial long nycto-period conditions; response time is about 8 to 8.5 weeks.

*Post-production longevity.*—Excellent post-production longevity; plants of the new Poinsettia maintain good substance and bract color for about four to six weeks; flower bracts persistent.

*Inflorescence diameter*.—About 25 cm.

*Inflorescence height*.—About 4 cm to 6 cm.

*Flower buds*.—Length: About 5 mm to 10 mm. Diameter: About 3 mm. Shape: Ovoid. Texture and luster: Smooth, glabrous; glossy. Color: Close to 140B.

*Flower bracts*.—Quantity per inflorescence: About 18 to 20. Length: About 8 cm to 12 cm. Width: About 8 cm. Shape: Ovate. Apex: Acuminate. Base: Cuneate. Margin: Entire; slightly undulate. Aspect: Horizontal to slightly drooping. Venation: Pinnate. Texture and luster, upper and lower surfaces: Moderately rugose, glabrous; matte. Color: Developing bracts, upper surface: Close to 45B. Developing bracts, lower surface: Close to 46D. Fully expanded bracts, upper surface: Close to 45A; venation, close to 45A; color does not change with subsequent development. Fully expanded bracts, lower surface: Close to 45B; venation, close to 45B; color does not change with subsequent development. Bract petioles: Length: About 2 cm. Diameter: About 3 mm. Texture and luster, upper and lower surfaces: Smooth, glabrous; semi-glossy. Color, upper and lower surfaces: Close to 46A.

*Cyathia*.—Quantity per corymb: About five to six. Length: About 3 mm to 5 mm. Width: About 4 mm. Shape: Ovoid. Texture and luster, inner and outer surfaces: Smooth, glabrous; matte. Color, developing, inner surface: Close to 141C. Color, developing, outer surface: Close to 141B. Color, fully developed, inner surface: Close to 143B. Color, fully developed, outer surface: Close to 143A. Nectaries: Quantity per cyathium: Typically one. Length: About 3 mm. Diameter: About 3 mm. Shape: Lip-shaped. Texture and luster, inner and outer surfaces: Smooth, glabrous; matte. Color, developing, inner and lower surfaces: Close to 17C. Color, fully developed, inner surface: Close to 17A. Color, fully developed, outer surface: Close to 17B.

*Pedicels*.—Length: About 1 mm to 3 mm. Diameter: About 1 mm to 2 mm. Strength: Moderately strong. Texture and luster: Smooth, glabrous; semi-glossy. Color: Close to 145A.

*Reproductive organs*.—Stamens: Quantity per cyathia: Numerous. Filament length: About 3 mm to 5 mm. Filament color: Close to 46A. Anther size: About 1 mm by 3 mm. Anther color: Close to 46A. Amount of pollen: Moderate. Pollen color: Close to 22A. Pistils: Quantity per cyathia: Typically one or two. Pistil length: About 4 mm. Style length: About 3 mm. Stigma diameter: About 1 mm. Stigma color: Close to 46A. Ovary color: Close to 138B. Fruits: Quantity per plant: None to very few. Length: About 8 mm to 12 mm. Diameter: About 6 mm to 10 mm. Texture: Smooth, glabrous. Color: Close to 47A.

Pathogen & pest resistance: To date, plants of the new Poinsettia have not been shown to be resistant to pathogens and pests common to Poinsettia plants.

It is claimed:

1. A new and distinct Poinsettia plant named 'LAZZPO1531' as illustrated and described.

* * * * *